United States Patent
Sim

(10) Patent No.: US 8,997,577 B2
(45) Date of Patent: Apr. 7, 2015

(54) METHOD AND APPARATUS FOR MEASURING RESIDUAL STRESSES IN A COMPONENT

(71) Applicant: Airbus Operations Limited, Bristol (GB)

(72) Inventor: Wei-Ming Sim, Bristol (GB)

(73) Assignee: Airbus Operations Limited, Bristol (GB)

( * ) Notice: Subject to any disclaimer, the term of this patent is extended or adjusted under 35 U.S.C. 154(b) by 260 days.

(21) Appl. No.: 13/646,095

(22) Filed: Oct. 5, 2012

(65) Prior Publication Data

US 2013/0091955 A1    Apr. 18, 2013

(30) Foreign Application Priority Data

Oct. 7, 2011   (GB) .................................. 1117343.2

(51) Int. Cl.
*G01N 19/06*    (2006.01)
*G01N 3/58*    (2006.01)
*G01L 5/00*    (2006.01)

(52) U.S. Cl.
CPC ................ *G01N 3/58* (2013.01); *G01L 5/0047* (2013.01)

(58) Field of Classification Search
CPC ........... G01L 5/0047; G01N 2203/008; G01N 2203/0005; G01P 15/0802; G01B 17/04

USPC .............................. 73/760, 769, 788, 796, 783
See application file for complete search history.

(56) References Cited

U.S. PATENT DOCUMENTS

| | | | |
|---|---|---|---|
| 3,802,316 A | | 4/1974 | Bohm et al. |
| 4,000,644 A | * | 1/1977 | Oppenheimer ................. 73/791 |
| 4,567,774 A | * | 2/1986 | Manahan et al. ............... 73/826 |
| 4,748,854 A | * | 6/1988 | Rao ................................. 73/799 |
| 5,193,395 A | * | 3/1993 | Chern et al. .................... 73/779 |
| 6,415,486 B1 | * | 7/2002 | Prevey, III .................... 29/90.01 |
| 6,470,756 B1 | * | 10/2002 | Prime ............................. 73/799 |
| 6,732,591 B2 | * | 5/2004 | Miles et al. .................... 73/808 |
| 7,319,126 B2 | * | 1/2008 | Laubry et al. ................. 526/335 |
| 7,320,242 B2 | * | 1/2008 | Hoo Fatt et al. ............. 73/12.14 |
| 7,373,802 B2 | * | 5/2008 | Powers et al. ................ 73/12.09 |
| 7,472,603 B2 | * | 1/2009 | Kim ................................ 73/823 |

FOREIGN PATENT DOCUMENTS

JP    6-102107    4/1994
JP    2007-303916    11/2007

OTHER PUBLICATIONS

Search Report for GB 1117343.2 dated Feb. 2, 2012.

* cited by examiner

*Primary Examiner* — Max Noori
(74) *Attorney, Agent, or Firm* — Nixon & Vanderhye P.C.

(57) ABSTRACT

A process for measuring the through stress distribution (12) in a workpiece (10) by taking progressive cuts (14, 16) and measuring the deflection of the workpiece at the cut point.

11 Claims, 3 Drawing Sheets

METHOD AND APPARATUS FOR MEASURING RESIDUAL STRESSES IN A COMPONENT

This application claims priority to GB 1117343.2 filed 7 Oct. 2011, the entire contents of each of which are hereby incorporated by reference.

The present invention is concerned with a method of measuring residual stresses in a component. More specifically, the present invention is concerned with a method of measuring through-thickness residual stresses in a engineering components, particularly of metal, which stresses have arisen from a manufacturing operation such as roll forming.

Manufacturing operations such as roll forming produce through-thickness residual stresses in components. Such stresses are not immediately apparent because they tend to be symmetrical through the thickness of the billet (and therefore produce no net strain). Residual stresses are problematic when the component is in-use because applied loading may cause stresses within the component which are higher than expected. Further, if the component is to be machined to size post-rolling, residual stresses may cause unexpected distortion following machining.

It is beneficial to be able to measure these residual stresses, so that they can be taken into account when the component is in use, or subsequently machined. This avoids any unexpected shortening of component life because of unexpectedly high stresses, and also allows the residual stresses to be accounted for when the component is manufactured to avoid distortion.

Known methods of measuring residual stresses involved techniques such as slitting and deep hole drilling, in which a strain gauge is used to measure the strain within the component and as such determine the residual stress at that point. These techniques require specialist equipment and strain gauges, both of which are not generally available in a manufacturing environment, and instead are laboratory based systems. Therefore the determination of a residual stress field is a time consuming and costly process involving transport of the component to be examined to a suitable facility.

It is an aim of this invention to mitigate the above disadvantages by providing a method which can be applied using existing manufacturing equipment, and does not require significant specialist equipment.

According to a first aspect of the present invention there is provided a method of measuring through-thickness residual stresses in a component comprising the steps of:
clamping the workpiece at a first position and a second position, spaced from the first position,
performing a first material removal operation at a third location intermediate the first and second locations,
releasing the workpiece at the second position,
measuring a first deformation of the workpiece,
determining residual stresses in the workpiece from the first deformation.

Preferably the method comprises the steps of, following the step of measuring the deformation of the workpiece:
re-clamping the workpiece at the second position,
performing a further material removal operation at the third location,
measuring a further deformation of the workpiece following the further material removal operation,
determining further residual stresses in the workpiece from the further deformation.

Preferably the steps of re-clamping, further material removal, further measurement and determination of further stresses are repeated to form a through-thickness residual stress distribution in the workpiece.

Preferably the step or steps of measuring are performed at the third position.

According to a second aspect of the present invention there is provided an apparatus for measurement of residual through-thickness stresses in a metallic component comprising:
a first clamp,
a second clamp spaced from the first clamp,
a machine tool configured to perform a material removal operation on a workpiece held by the clamps, at a position between the clamps,
a deflection measurement apparatus positioned between the first and second clamps.

Preferably the deflection measurement apparatus is positioned at the same position between the clamps as the machine tool.

Preferably the deflection measurement apparatus is arranged to be positioned on an opposite side of the workpiece to the machine tool in use.

An example process and apparatus according to the present invention will now be described with reference to the following drawings, in which:—

Figure 1:
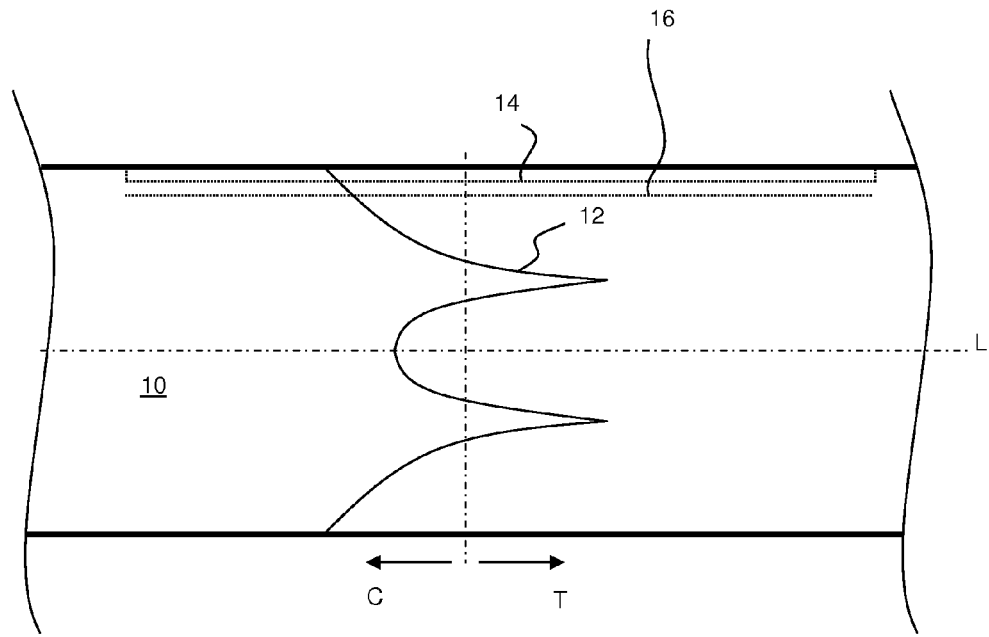
FIG. 1 is a schematic side section view of an example workpiece showing an example stress distribution.

Turning to FIG. 1, a workpiece 10 has been formed by a known manufacturing process such as roll forming. A stress plot 12 shows how the residual stresses vary throughout the thickness of the workpiece 10, ranging from compression (C) to tension (T). As can be seen, the stress plot is symmetrical about the longitudinal axis of the workpiece L and, as such, the stresses are balanced such that the workpiece is geometrically stable in this condition (in other words the residual stresses are not observable from a deformation in the material).

According to the invention, performing a machining operation by taking cuts as shown by cut lines 14 and 16, will produce an asymmetric stress distribution 12 and therefore, consequently, a deflection of the workpiece 10. The asymmetry of the stress distribution as a result will induce bending stress upon the workpiece 10. By releasing the workpiece and allowing it to deform under the asymmetric stress, the degree of residual strain can be measured.

Figure 2:
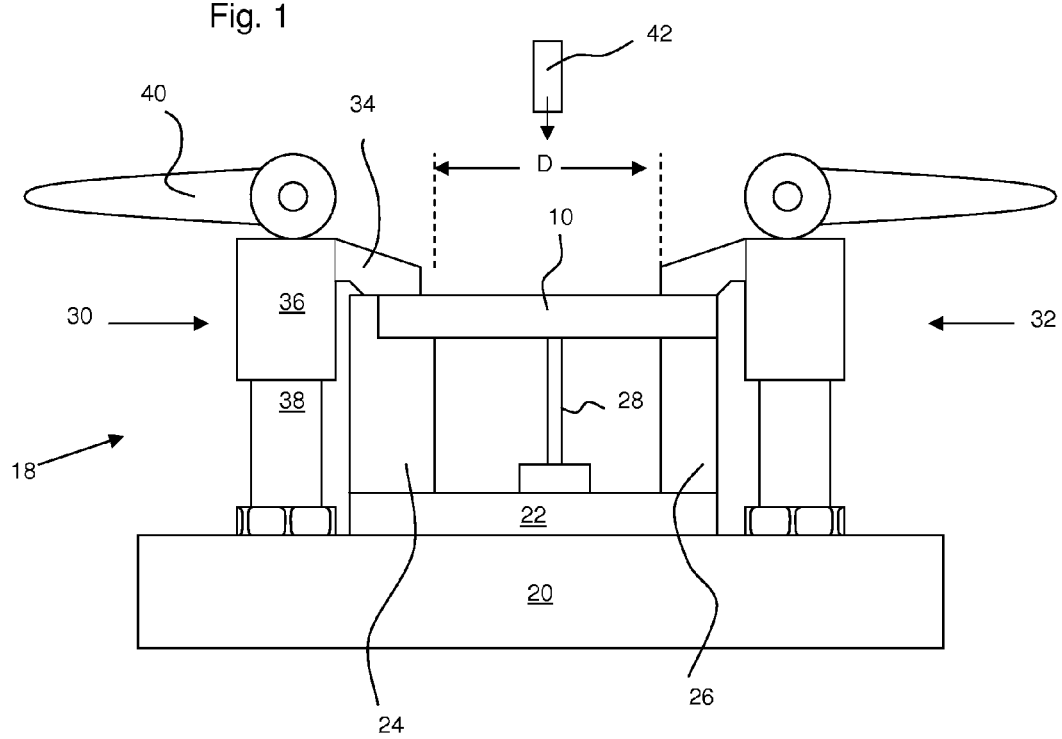
FIG. 2 is a schematic side view of an apparatus in accordance with the second aspect of the present invention.

Turning to FIG. 2, an apparatus 18 for performing the method of the present invention is shown.

A machine table 20 has a jig base 22 installed thereon, having a first support 24 and a second support 26 extending at opposite ends thereof. The supports 24, 26 are spaced apart by a distance D and are configured to receive the workpiece 10 (for example their relative spacing may be adjustable to provide a suitable support for the workpiece 10). Each support 24, 26 vertically supports the workpiece 10.

A deflection probe 28 extends from the jig base 22 upwardly into contact with the workpiece 10 at a position intermediate the supports 24, 26, and is arranged to measure any deflection in the workpiece.

On either side of the first and second supports 24, 26, adjustable clamp assemblies 30, 32 respectively are provided.

Each clamp assembly 30, 32 comprises a clamp member 34 arranged to clamp the workpiece 10 between it and the relevant support. The clamp member 34 is connected to a cylinder 36 which sits on a piston 38 and can be moved up and down by a lever 40 in order to clamp and release the workpiece 10.

A machine tool 42 can be lowered onto the upper surface of the workpiece 10 at the corresponding position to the deflection probe 28. The machine tool 42 is capable of taking sequential cuts of a known distance into the workpiece 10 and, as such, comprises a motion transducer in order to record the depth of cut into the workpiece 10.

It will be noted that one or both of the clamps 32 may be automatically activated by a computer controlled actuator, as will be described in more detail below.

Figure 3:
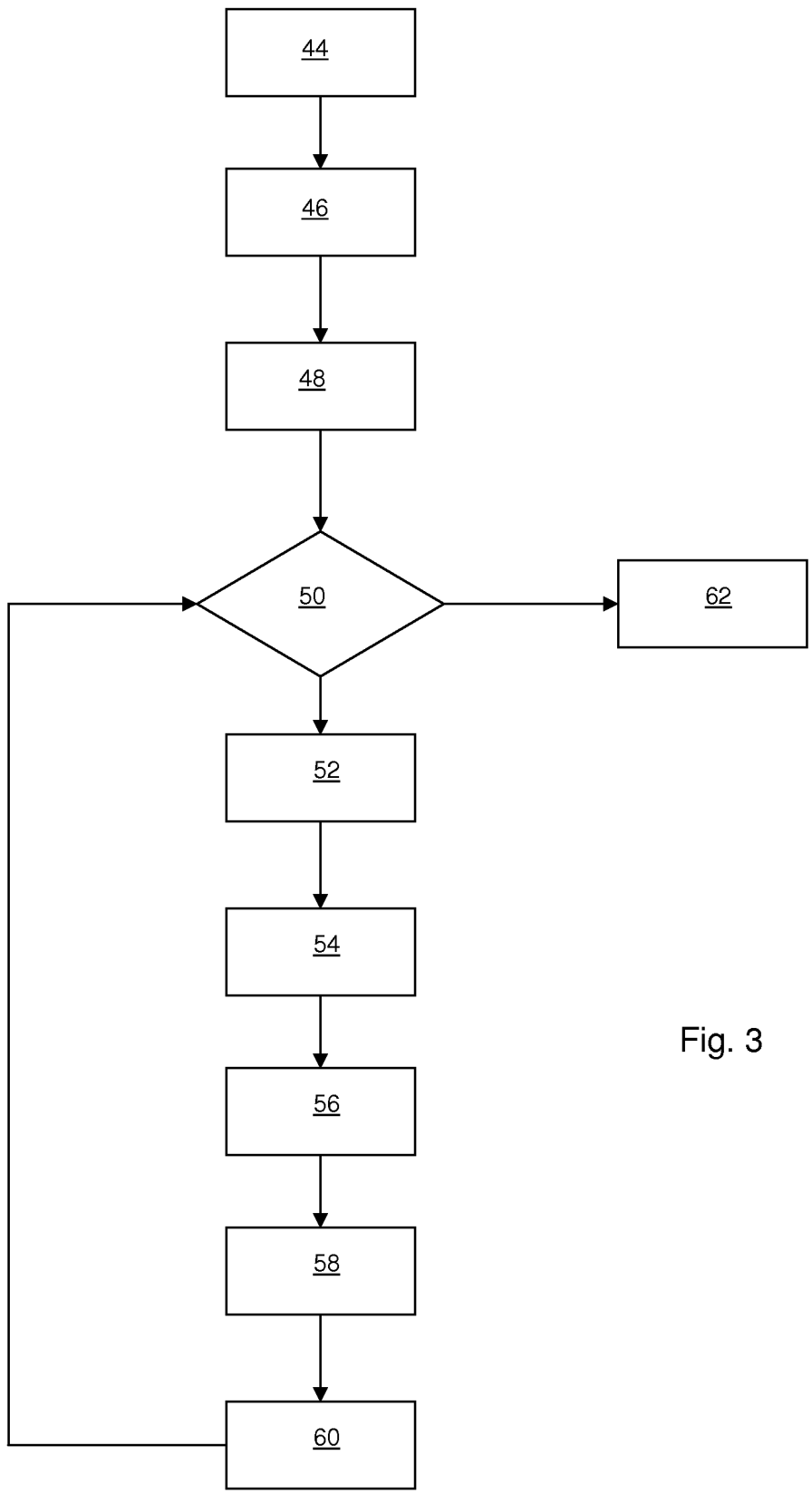
FIG. 3 is a process diagram of a method in accordance with the present invention.

Turning to FIG. 3, an example method in accordance with the present invention is shown as a flow diagram.

At step 44, the jig and workpiece are set up such that the workpiece 10 is clamped within the apparatus 18.

At step 46, cutting conditions are manually inputted into the machining sensor or control computer. By way of example, the system may be configured to take N=50 cuts of d=1 mm each.

At step 48, the count variable n is initialised at n=1.

At step 50, the value of n is interrogated to check whether n=N (i.e. whether the system has reached the desired number of cuts).

At step 52, n is multiplied by the depth of cut d, and the machine tool 42 is advanced into the workpiece 10 by a distance of n×d from the workpiece's original top surface datum.

At step 54, the clamp 32 is released by the control computer.

At step 56, the deflection probe 28 is used to measure the deflection of the workpiece 10. This is stored in the computer.

At step 58, clamp 32 is reapplied such that the deflection probe returns to zero.

At step 60, n=n+1, at which point the process returns to step 50. At step 50, should n=N (the maximum number of cuts requested) then the process moves onto step 62, at which point it ends.

Following the aforementioned process, a number of deflections for each value of n is achieved. The residual stresses within the material can be calculated for each of these deflections and, as such, a profile of the stress distribution throughout the workpiece 10 can be obtained. It will be noted for symmetrical stress distributions as seen in FIG. 1, only half of the thickness of the material 10 needs to be machined.

Figure 4:
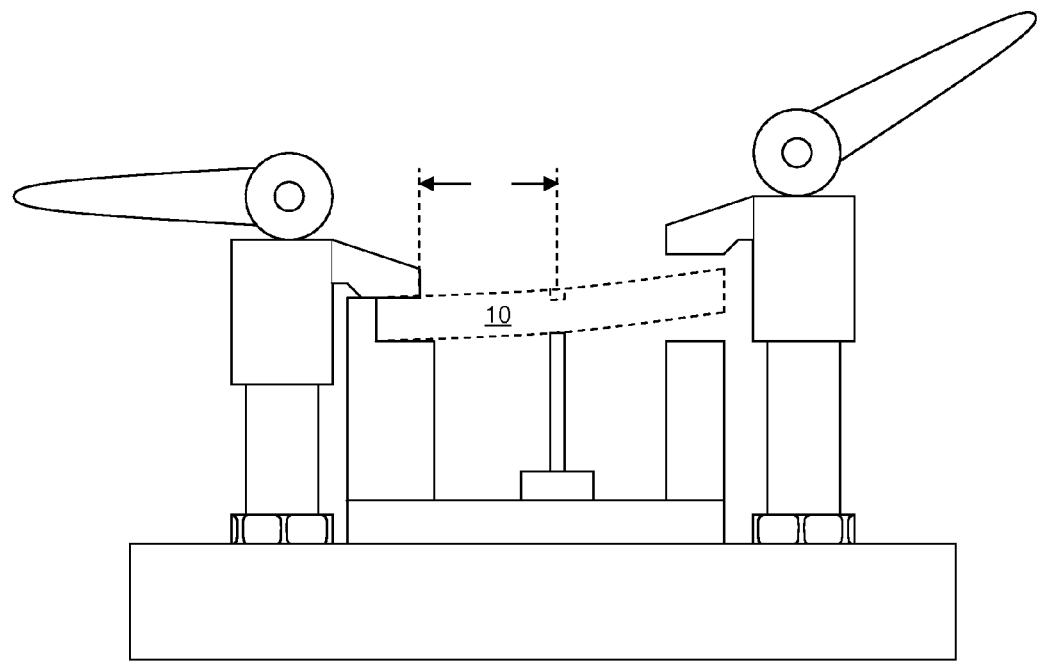
FIG. 4 is a schematic side view of the apparatus of FIG. 2 in use.
Figure 5:
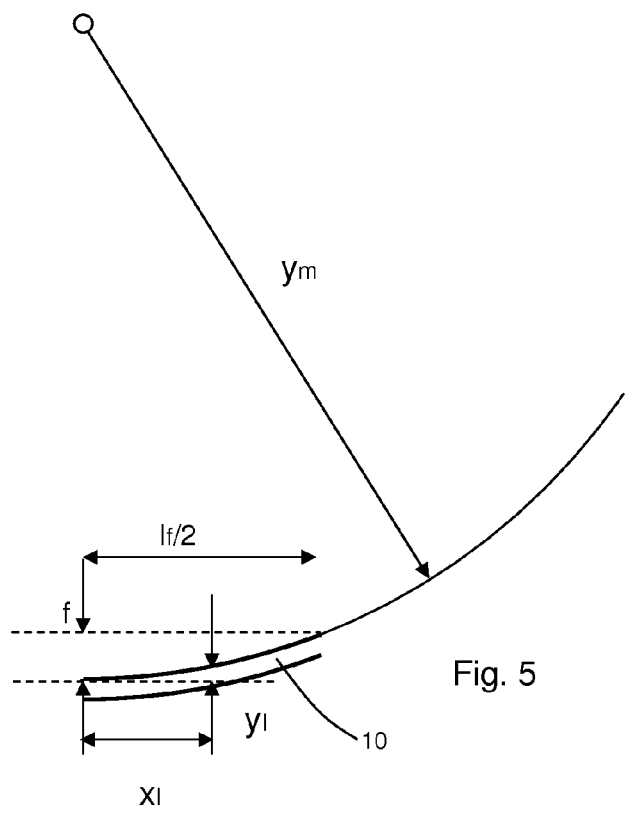
FIG. 5 is a side view representation of workpiece deflection.

The stresses throughout the workpiece may be calculated as follows:

Referring to FIGS. 4 and 5, the deflection of the workpiece 10 is assumed to approximate to a circle segment governed by the general equation $r^2 = x^2 + y^2$.

If the radius of curvature is $y_m$, as shown in FIG. 5, the measurement is taken at distance $x_l$ from the left hand clamp and $y_l$ is the measured displacement then:

$$y_m^2 = x_l^2 + (y_m - y_l)^2$$
$$=> y_m^2 = x_l^2 + y_m^2 - 2y_m y_l + y_l^2$$
$$=> 2 y_m y_l = x_l^2 + y_l^2$$
$$=> y_m = \frac{x_l^2}{2 y_l} + \frac{y_l}{2}.$$

In order to obtain f, which is the maximum deformed distance from the reference for a given reference length of specimen lf:

$$y_m^2 = \left(\frac{l_f}{2}\right)^2 + (y_m - f)^2$$
$$=> y_m^2 = \left(\frac{l_f}{2}\right)^2 + y_m^2 - 2 y_m f + f^2$$
$$=> f = y_m + \sqrt{y_m^2 - \left(\frac{l_f}{2}\right)^2}$$

Therefore, using the measured deformation at a point along the workpiece 10, the maximum deformed distance can be calculated.

Using the maximum deflection of the workpiece, the residial stresses at the cut depth can then be calculated.

Variations fall within the scope of the present invention. The process may be controlled by a CNC system in which control is passed to the apparatus shown in FIG. 2 and the results, i.e. deflection measurements, are fed back to the PC for analysis.

Alternatively, the process can be undertaken manually with the user manually clamping and unclamping the clamp 32 and taking appropriate measurements using a manual measuring apparatus, reclamping and remachining.

The process may be used on vertical and horizontal bed tables.

The invention claimed is:

1. A method of measuring through-thickness residual stresses in a workpiece comprising the steps of:
   clamping the workpiece at a first position and a second position, said second position is spaced from the first position;
   after clamping, performing a first material removal operation at a third position located intermediate the first and second positions;
   after said performing step, releasing the workpiece at the second position;
   after said releasing step, measuring a first deformation of the workpiece; and,
   determining residual stresses in the workpiece from the first deformation measurement.

2. A method according to claim 1 comprising the steps of, following the step of measuring the deformation of the workpiece:
   re-clamping the workpiece at the second position;
   performing a further material removal operation at the third position;
   measuring a further deformation of the workpiece following the further material removal operation; and
   determining further residual stresses in the workpiece from the further deformation.

3. A method according to claim 2 in which the steps of re-clamping, further material removal, further measurement and determination of further stresses are repeated to form a through-thickness residual stress distribution in the workpiece.

4. A method according to claim 1 in which the step of measuring is performed at the third position.

5. A method according to claim 1 in which the step of determining the residual stresses comprises the step of calculating a maximum deformation of the workpiece at a position other than the measurement position.

6. An apparatus for measurement of residual through-thickness stresses in a workpiece comprising:

a first clamp configured to clamp said workpiece at a first position;

a second clamp spaced from the first clamp and configured to clamp said workpiece at a second position;

a machine tool configured to perform a material removal operation on said workpiece held by the clamps, at a third position between said first and second clamps;

a deflection measurement apparatus configured to measure deflection of said workpiece at a location between the first and second clamps; and based upon said measured deflection, computing the residual through-thickness stress.

7. An apparatus for measurement according to claim 6, wherein the deflection measurement apparatus is positioned at the third position.

8. An apparatus for measurement according to claim 7 in which the deflection measurement apparatus is arranged to be positioned on an opposite side of the workpiece from the machine tool.

9. A method of measuring through-thickness residual stresses in a workpiece comprising the steps of:

clamping the workpiece at a first position and a second position, spaced from the first position;

performing a first material removal operation at a third location intermediate the first and second locations;

releasing the workpiece at the second position;

measuring a first deformation of the workpiece; and determining residual stresses in the workpiece from the first deformation, wherein the step of determining the residual stresses comprises the step of calculating a maximum deformation of the workpiece at a position other than the measurement position.

10. An apparatus for measurement of residual through-thickness stresses in a metallic workpiece comprising:

a first clamp;

a second clamp spaced from the first clamp;

a machine tool configured to perform a material removal operation on a workpiece held by the clamps, at a position between the clamps; and a deflection measurement apparatus positioned between the first and second clamps, wherein the deflection measurement apparatus is positioned at the same position between the clamps as the machine tool.

11. An apparatus for measurement of residual through-thickness stresses in a metallic workpiece according to claim 10 in which the deflection measurement apparatus is arranged to be positioned on an opposite side of the workpiece from the machine tool.

\* \* \* \* \*